United States Patent [19]

Wakizaka et al.

[11] 4,292,157

[45] Sep. 29, 1981

[54] SOLID POLE OXYGEN SENSOR AND ITS MANUFACTURING PROCESS

[75] Inventors: Hiroshi Wakizaka, Toyota; Hiroshi Shinohara, Okazaki; Yasuhiro Otsuka; Shinichi Matsumoto, both of Toyota, all of Japan

[73] Assignee: Toyota Jidosha Kogyo Kabushiki Kaisha, Aichi, Japan

[21] Appl. No.: 91,883

[22] Filed: Nov. 7, 1979

[30] Foreign Application Priority Data

May 18, 1979 [JP] Japan ................................. 54/61250

[51] Int. Cl.³ ............................................ G01N 27/58
[52] U.S. Cl. ............................ 204/195 S; 29/592 R
[58] Field of Search ............... 204/195 S, 1 S; 29/592

[56] References Cited

U.S. PATENT DOCUMENTS

| 3,719,574 | 3/1973 | Richardson | 204/195 S |
| 3,883,408 | 5/1975 | Kim et al. | 204/195 S |
| 4,035,277 | 7/1977 | Hennessy et al. | 204/195 S |
| 4,045,319 | 8/1977 | Deportes et al. | 204/195 S |
| 4,208,265 | 6/1980 | Hori et al. | 204/195 S |

FOREIGN PATENT DOCUMENTS 2742279  3/1978  Fed. Rep. of Germany ... 204/195 S

Primary Examiner—G. L. Kaplan
Attorney, Agent, or Firm—Stevens, Davis, Miller & Mosher

[57] ABSTRACT

A solid pole oxygen sensor in which one end of a lead wire of platinum or platinum/rhodium is buried in a solid pole and the surfaces of the solid pole and the lead wire are coated with an electroconductive paste. The solid pole is wrapped or encased in a solid electrolyte, pressure-molded into a pellet, which is dried and then fired in a reducing atmosphere. The surface of the sintered mass thus obtained is then plated or baked to form a platinum electrode, and the oxygen sensor element thus obtained is fitted or secured to the tip of an approximately cylindrical ceramic insulator equipped with electroconductive zones to be connected to the platinum electrode.

14 Claims, 18 Drawing Figures

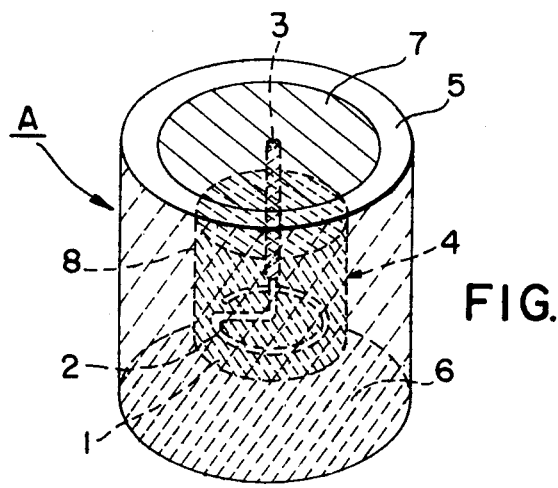
FIG. 2A
FIG. 2B
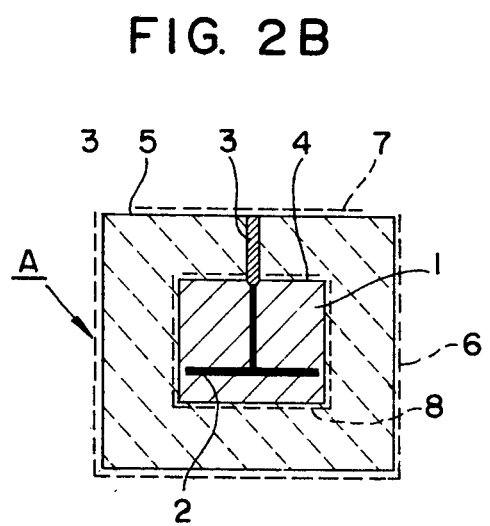
FIG. 2C
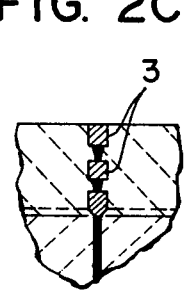

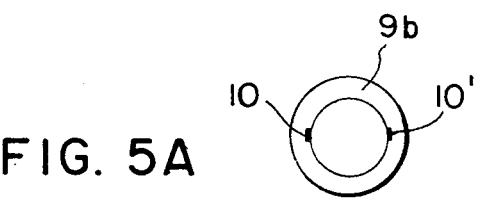
FIG. 5A
FIG. 4
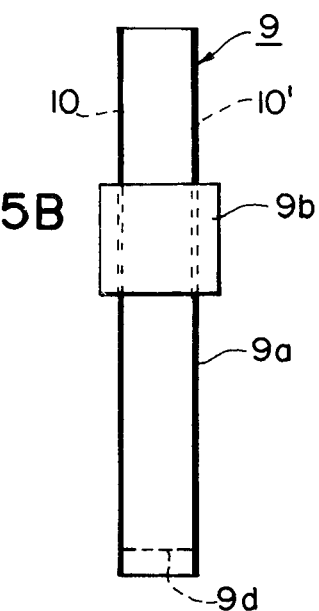
FIG. 5B
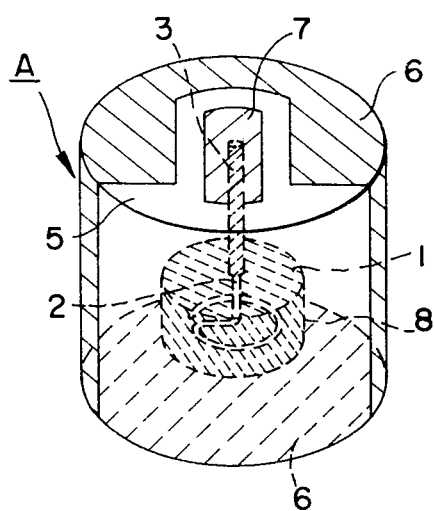
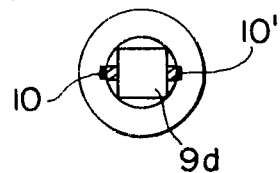
FIG. 5C

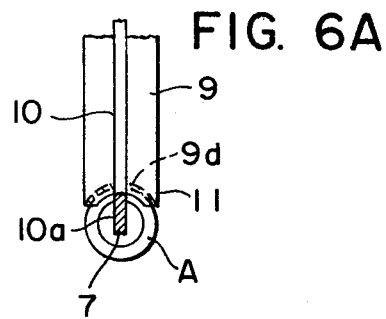
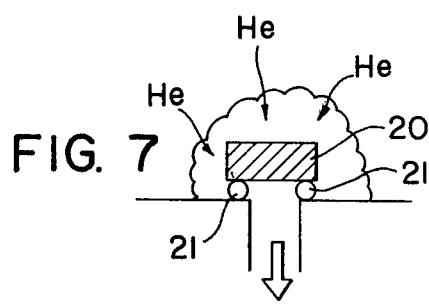
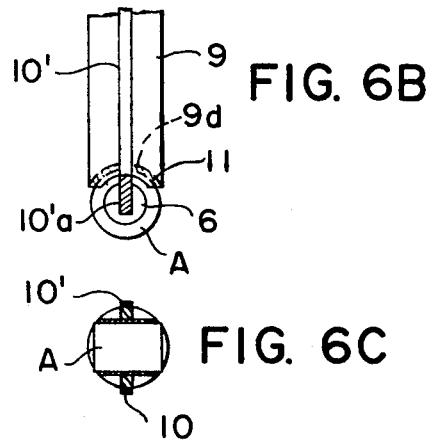
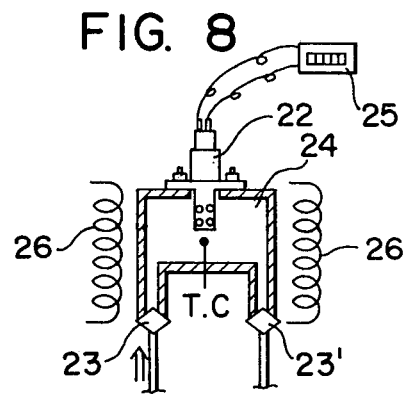
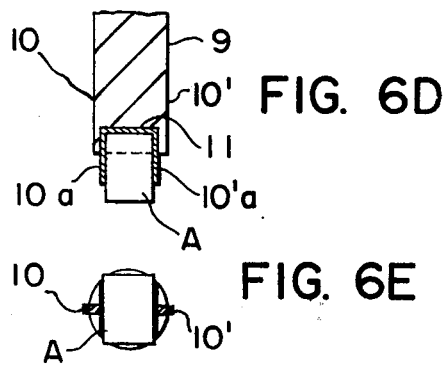
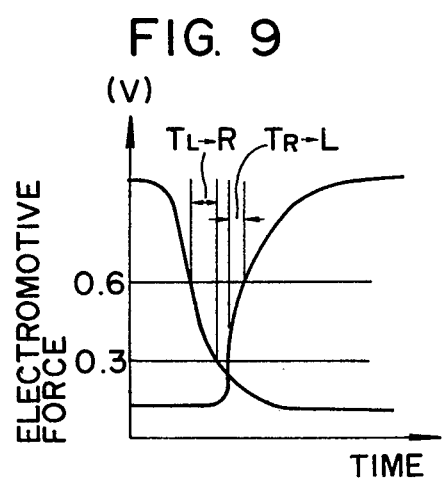

SOLID POLE OXYGEN SENSOR AND ITS MANUFACTURING PROCESS

BACKGROUND OF THE INVENTION

1. Field of the Invention

The present invention relates to a solid pole oxygen sensor and its manufacturing process.

The oxygen sensor is a means of measuring the equilibrium oxygen partial pressure in, say, the exhaust gas from an automotive engine.

2. Description of the Prior Art

Prior art oxygen sensors have a solid electrolyte vessel made of a solid electrolyte such as zirconia stabilized by yttrium oxide, etc. On the outside and inside surfaces of this vessel are formed internal and external electrode layers of platinum or platinum alloy film. The vessel is filled with an internal reference substance, i.e., a gas with a constant oxygen content such as air or a solid with a constant equilibrium oxygen partial pressure such as a mixed powder of metal-metal oxide.

The ratio between the equilibrium oxygen partial pressures of a gas to be measured, which comes into contact with the external electrode layer and the internal reference substance which is in contact with the internal electrode layer is converted to an electromotive force, by which the equilibrium oxygen partial pressure in the gas to be measured can be determined. As the internal reference substance in the oxygen sensor, a gas or a solid is available. Functionally and structurally, the solid has been found to be better than the gas, when it is to serve as part of automotive equipment.

The conventional solid pole oxygen sensor, including a solid electrolyte vessel which involves a difficult step of calcining or high-temperature firing for manufacture, is complicated in structure and unfit for miniaturization. Moreover, it is difficult to take out of the vessel the potential of the internal electrode layer in the solid electrolyte vessel.

BRIEF SUMMARY OF THE INVENTION

The primary object of the present invention is to provide a solid pole oxygen sensor which is simplified in structure and fit for miniaturization.

Another object of the present invention is to provide a solid pole oxygen sensor which maintains excellent performance even after long service.

A further object of the present invention is to provide a solid pole oxygen sensor in which one end of a Pt or Pt-Rh lead wire is buried in a solid pole, the surface of the solid pole is coated with an electroconductive paste, the solid electrode thus constituted is wrapped or encased in a solid electrolyte, pressure-molded and dried, the molded product thus obtained is fired in a reducing atmosphere and Pt-electrodes are formed on the surface of the sintered mass obtained, thereby yielding an oxygen sensor element. The oxygen sensor element is joined to the tip of an approximately cylindrical ceramic insulator provided with electroconductive zones to be connected to the Pt-electrodes.

A further object of the present invention is to provide a manufacturing process for a solid pole oxygen sensor in which that one end of a Pt or Pt-Rh lead wire is buried in a solid pole, the surface of the solid pole is coated with an electroconductive paste, the solid electrode thus constituted is wrapped or encased in a solid electrolyte, pressure-molded under 600-2000 Kg/cm$^2$ and dried, the molded product is fired at about 1350°-1500° C. in a reducing atmosphere, Pt-electrodes are formed by plating or baking on the surface of the sintered mass thus obtained, and the oxygen sensor element thus yielded is joined to the tip of an approximately cylindrical ceramic insulator provided with electroconductive zones to be connected to said Pt-electrodes.

BRIEF DESCRIPTION OF THE DRAWINGS

FIG. 2a is a perspective view of the oxygen sensor element;

FIG. 2b is a cross-sectional of FIG. 2a;

FIG. 2c is an enlarged sectional view of the lead wire coated with a sealing agent shown in FIGS. 2a and 2b;

FIG. 3b is a cross-sectional view of FIG. 3a;

FIG. 4 is a perspective view of still another embodiment of the oxygen sensor element;

FIG. 5a is a top plan view of the ceramic insulator;

FIG. 5b is a front elevational view of FIG. 5a;

FIG. 5c is a bottom plan view of FIG. 5b;

FIGS. 6a and 6b are enlarged side views of the junction between the sensor element A and the insulator 9 as viewed from the positive side and the negative auxiliary side electrodes;

FIG. 6c is a bottom plan view of FIGS. 6a and 6b;

FIG. 6d is a front elevational view of FIGS. 6a and 6b;

FIG. 6e is a bottom plan view of FIG. 6d.

FIG. 7 is a diagram showing the He-leak test;

FIG. 8 is a diagram showing the autoclave method; and

FIG. 9 is a graph illustrating the response characteristic of the oxygen sensor.

DETAILED DESCRIPTION OF THE INVENTION

Figure 1:
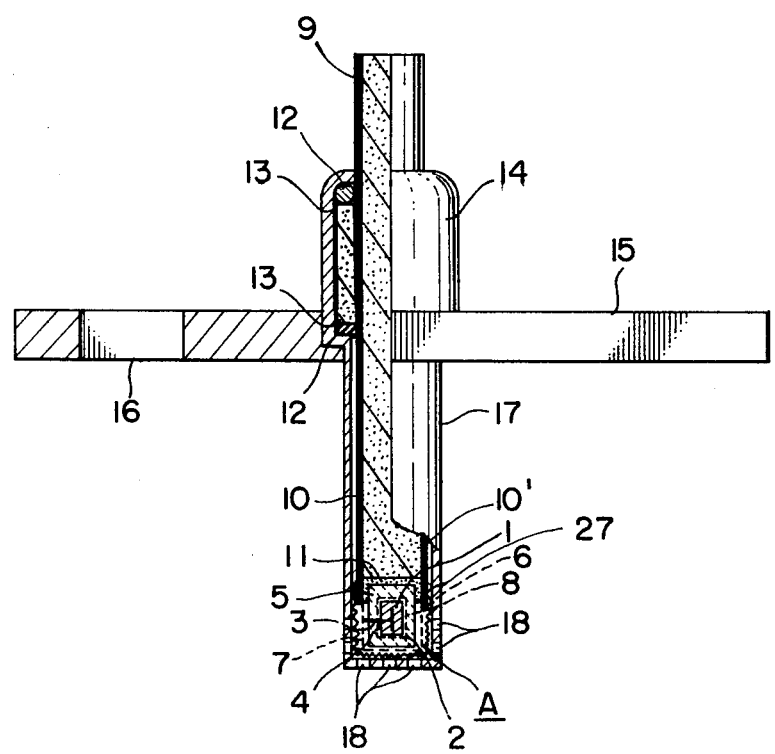
FIG. 1 is a side view partly in section showing the structure of a solid pole oxygen sensor according to the present invention.

As illustrated in FIG. 1, the oxygen sensor A according to the present invention includes a lead wire 2, having a diameter of 0.05–0.5 mm$\phi$ and made of Pt or Pt-Rh, which is buried in a solid pole 1. The surface of the solid pole 1 is coated with an electroconductive paste. The surface of the lead wire 2 is coated with a sealing agent 3. An internal negative electrode 8 is formed on the surface of the solid pole 1, thereby constituting a solid electrode 4. The solid electrode 4 is wrapped or encased in a solid electrolyte 5, which is molded into a pellet under a pressure of 600–2000 Kg/cm$^2$, preferably, under a pressure of 600–1200 Kg/cm$^2$, and dried. The molded pellet is then fired at about 1350°–1500° C. in a reducing atmosphere. The sintered mass thus obtained has a positive electrode 6 and a negative (auxiliary) electrode 7 formed on its surface by means of plating or baking to form the oxygen sensor element A. The oxygen sensor element A is fitted or secured, by means of a bonding agent 11, to the tip of an approximately cylindrical ceramic insulator 9 having electroconductive zones 10, 10′ provided longitudinally, which are respectively connected to the positive electrode 6 and the negative auxiliary electrode 7. Then, the surface of the oxygen sensor element is provided with a spinel coating layer 27 of MgAl$_2$O$_4$ (50–150$\mu$) which is formed by plasma spray coating.

Finally, the assembly thus obtained is mounted on a holder consisting of a housing 14, a flange 15 having a fitting hole 16 therein, and a protective cover 17 having ventilation holes 18 therein. As shown in FIG. 1, a metal packing 12 and a filler 13 are positioned between the ceramic insulator 9 and the housing 14.

The solid pole 1 in the oxygen sensor element A according to the present invention is made of a metal and its oxide, for instance, Co/CoO, V/VO, Fe/FeO, etc. to which other additives such as an anti-sinter agent, a foaming agent and the like, are added in adequate appropriate quantities.

As the anti-sinter agent, the same substance as the solid electrolyte 5, for instance, $ZrO_2$ stabilized with $Y_2O_3$, is preferable. As the foaming agent, a substance which sublimates at a low temperature of less than 100° C. is available. When Fe/FeO is utilized as the solid pole 1, the composition will be: Fe (carbonium decomposed iron powder) - - - 45% by weight; 5.5 mol % $Y_2O_3$-$ZrO_2$ - - - 10% by weight; and the foaming agent will consist of $NH_4HCO_3$ - - - 45% by weight.

Further, for the purpose of improving the activity of the solid pole 1, a small volume of platinum black, say, 2% by weight, can be added as the activating agent.

The lead wire 2 should be fine but not so fine as to be liable to snap or break apart. The diameter of the lead wire 2 may be 0.05–0.5 mm$\phi$, and more desirably 0.05–0.2 mm$\phi$. If the wire diameter is large, the surface area will increase, resulting in poor sinterability of the surrounding solid electrolyte. If the wire diameter is too small, the desired sinterability will be achieved but the wire will become liable to snap or break apart.

The lead wire 2 is made of Pt or Pt-Rh. When the lead wire 2 is made of Pt-Rh, it is desirable that an additional amount of Rh to Pt be provided of for example 10–30% by weight with the optimum value of 15–25% by weight. At less than 10% by weight, the heat resistance drops, causing the wire to snap or break apart. At more than 35% by weight, the durability increases but the ductility and flexibility of the wire deteriorate, resulting in inadequate workability.

The sealing agent 3 to be applied around the lead wire 2 buried in the solid pole 1 or around the projection of the lead wire 2 from the solid pole 1 is a combination of an electroconductive metal, such Pt or a Pt-Rh alloy and an organic binder. The organic binder may be ethylcellulose+butyl carbitol acetate (BCA) or nitrocellulose+butyl acetate is blended with more than 15% by weight, desirably 15–20% by weight of Pt. The organic binder employed is desirably one based on nitrocellulose, which is easier to eliminate through heating.

The conventional solid pole oxygen sensor is sealed with a glass sealant which can leak and perform inadequately in a high-temperature durability test.

The sealant used in the present invention is an electroconductive paste, such as metallic paste, which, together with Pt metallization, produces excellent sealing and performs well with no gas leakage.

The solid electrolyte 5 is $ZrO_2$ stabilized with 4–10 mol% of $Y_2O_3$. A partially stabilized $ZrO_2$ is desirable from the standpoint of resistance to heat shock and $ZrO_2$ with a low mol % content of $Y_2O_3$ is desirable for the purpose of low-temperature firing. The anti-sinter agent, which is listed above, to be added to the solid pole 1 is desirably the same material as the solid electrolyte 5.

For pelletization of the sensor element A, a handpress is applied to the solid electrode 4 wrapped in the solid electrolyte 5 in a specified metal mold under a molding pressure of 600–2000 Kg/cm$^2$. Under a molding pressure of more than 2000 Kg/cm$^2$, removal of air out of the molded product is insufficient. As a result, air bubbles are left in the sintered mass and the quality of the finished product is poor.

The pelletized sensor element A is dried at 200° C. in the atmosphere for 15–30 minutes to drive the organic binder out of the sealing agent. The drying temperature in the oxidizing atmosphere is 300° C. at the most and the drying time will naturally be shortened under a reduced pressure.

Maximum pressure reduction is 100 mmHg. Further reduction will not be effective, because it causes a change in the molded product.

Firing of the molded pellet is carried out at a high temperature of 1350°–1500° C. for 2–3 hours in an electric furnace in a reducing atmosphere of inert gas such Ar or $N_2$ with a small amount (0.5–2% by volume) of a reducing gas such as $H_2$. Although as a general rule, product quality increases with firing temperature, when the prevention of sintering, particle growth of the solid pole and deterioration of the lead wire is considered, the firing temperature is desirably lower than the sintering temperature of the solid pole and thus the abovementioned range is found optimum. It is particularly necessary that the temperature be one at which a strong sintering of the solid pole 1 does not take place or one at which the metal of the solid pole 1 will not melt. Sintering time depends on the kind of solid electrolyte 5 employed and the sintering treatment is carried out until the water absorption in the sintered means becomes 0% (as measured according to JIS R 2205). Since it is not desirable for sinterability to raise the temperature in a short time, i.e., very quickly, the adequate rate of temperature elevation is 100°–300° C./hr.

The positive electrode 6 and the negative auxiliary electrode 7 on the surface of the solid electrolyte are made of Pt or Pt and another element of the platinum family. They can be made by Pt plating, Pt paste application baking, chloroplatinic acid-baking, ion plating, etc. The plating method is recommended. The negative (solid pole) electrode 8 around the solid pole should be made of the same material as the sealing agent.

Examples of electrode manufacture are given below.
Platinum plating:

| Pretreatment | etching (hydrofluoric acid) | 30 min. |
|---|---|---|
| | ultrasonic washing | 3 min. |
| | immersion in platinum solution | 10 min. |
| | drying at room temperature | 8 hr. |
| Surface reduction (by commercial reducing agent) | | 10 min. |
| Pt chemical plating | surface resistance | 5 Ω |
| Pt electric plating | less than 1 Ω for film thickness 1μ | |

Chloroplatinic acid baking:

The element is dipped into a solution of chloroplatinic acid in butylcarbitol, taken out of it and then dried. The dip-dry process is repeated until the surface resistance reaches about 1 Ω.

Platinum paste coating and baking:

The surface of the element, after being pretreated (degreased), is evenly coated with a commercially available Pt paste. After drying of the paste, the element is baked in the atmosphere at 950° C. for 10 minutes.

The oxygen sensor A according to the present invention is constituted as follows: As illustrated in FIGS. 2a and 2b, the tip of the lead wire 2 to be buried in the solid pole 1 is formed into a substantially circular configuration to suit the configuration of the solid pole 1. On the outside of the solid pole 1 is formed the negative electrode 8. The solid electrode 4 is wrapped or encased in the solid electrolyte 5 to pelletize it by pressing and the electrodes 6 and 7 are thus formed. The sealing agent 3 may be applied to the entire surface of the lead wire 2 or only partially along the surface (see FIG. 2c).

Figure 3A:
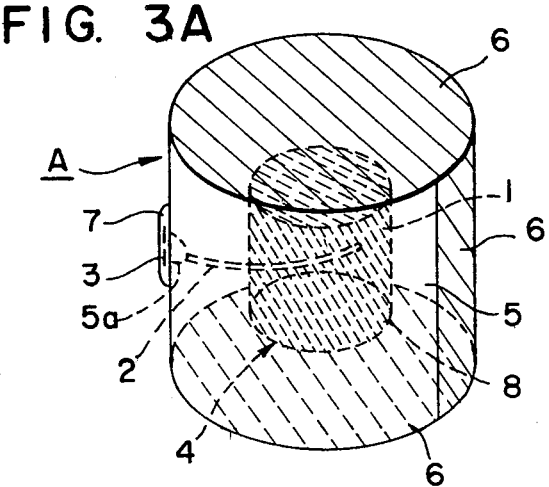
FIG. 3a is a perspective view of another embodiment of the oxygen sensor element.
Figure 3B:
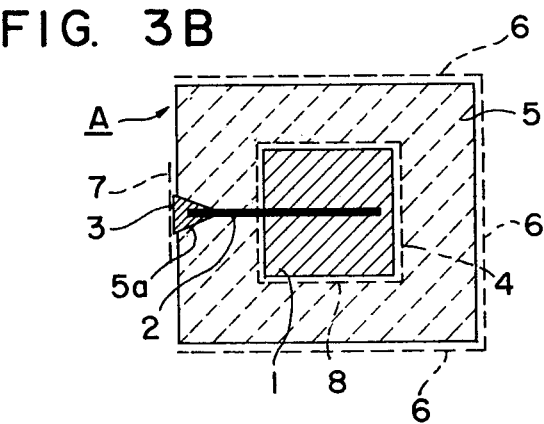

Another embodiment of the solid pole oxygen sensor element A according to the present invention is illustrated in FIGS. 3a and 3b. As seen in those figures, in this embodiment, the solid electrode 4 constituted by burying the tip of linear lead wire 2 in the solid pole 1 is wrapped or encased in a solid electrolyte 5 to form an integral unit. A recess 5a can be cut in the electrolyte 5 or it can be or is preliminarily molded to include the recess 5a. After sintering, with the lead wire 2 projecting slightly into the recess 5a, it is filled with the electroconductive sealing agent 3 and the electrodes 6 and 7 are formed. The lead wire 2 may also be buried in a direction in alignment with the longitudinal axis of the cylindrical solid pole 1 as shown in FIG. 2.

As for the electrode formed on the surface of the pelletized solid electrolyte 5, the negative auxiliary electrode 7 need only be formed at the area connecting to the lead wire 2 with the other area being the positive electrode 6 (note FIG. 3b). The area of the electrodes 6 and 7 need not be limited to the areas illustrated in FIGS. 2 and 3; for instance, they can be formed as shown in FIG. 4.

The ceramic insulator 9 to connect the oxygen sensor element A thus formed will now be described with reference to FIGS. 5a, 5b, 5c, 6a, 6b, 6c, 6d and 6e.

FIG. 5a is a top plan view, FIG. 5b is a front elevational view and FIG. 5c is a bottom plan view of the ceramic insulator 9. As seen from the drawings, a ring 9b is inserted into and bonded to the insulator 9 used with the present invention (FIGS. 1 and 6b) for housing within a holder. The ring 9b is positioned substantially midway along the elongated cylindrical body 9a of the insulator 9. Electroconductive zones 10, 10' are formed in parallel on the surface of the insulator 9. A concave camber 9d is formed in the insulator 9 on the bottom side thereof. The camber 9d is curved so as to fit the side profile of the sensor element A to be joined therewith.

An example of the pelletized sensor element A as joined to the insulator 9 is shown in FIGS. 6a, 6b, 6c, 6d and 6e. FIGS. 6a and 6b are enlarged side views of the junction between the sensor element A and the insulator 9 as viewed from the positive side and the negative auxiliary side electrodes; FIG. 6c is the corresponding bottom plan view; and FIG. 6d is front elevational view corresponding to FIGS. 6a and 6b; and FIG. 6e is a bottom plan view.

As seen from the drawings, the pelletized oxygen sensor element A has its side wall in direct contact with the recess 9d in the tip of the insulator 9, and has its circular ends with the electrodes 6 and 7 extending in the same direction as the electroconductive zones 10, 10'. The insulator 9 and the sensor element A are joined together with a bonding agent 11 so that one of the electroconductive zones 10 is connected to the negative auxiliary electrode 7 of the element A, and the other electroconductive zone 10' is connected to the positive electrode 6.

To assure more reliable connection between the zones 10 and 10' and the electrodes 6 and 7 on the oxygen sensor element A, as shown in FIGS. 6b and 6d, electroconductive substances 10a, 10"a, for example Pt paste, may be spread between them. The connection between the zones 10 and 10' on one side and the minus auxiliary electrode 7 and the positive electrode 6 on the other is effected by Pt paste baking.

The ceramic insulator 9 is made of an insulating material, such as $Al_2O_3$, $MgO \cdot Al_2O_3$ (spinel), forsterite, or mullite.

The electroconductive zones 10, 10' are made of Pt and these are formed on the surface of the insulator 9 by Pt paste baking or printing. The bonding agent 11 is desirably $CaO\text{-}Al_2O_3\text{-}MgO$, $SiO_2\text{-}CaO\text{-}Al_2O_3$, $SiO_2\text{-}CaO\text{-}Al_2O_3\text{-}MgO$, $SiO_2\text{-}MgO$, or $TiO_2\text{-}BaO$.

The housing 14, the flange 15 and the protective cover 17, which constitute the holder for the solid pole oxygen sensor according to the present invention, are made of stainless steel.

The sensor element A is fixed to the holder by hot-caulking in the air at, say, 600° C. The metal packing 12 used is a stainless steel ring or a copper ring. The filler 13 used is graphite, asbestos or pyrophyllite.

When a solid pole oxygen sensor according to the present invention is set in the path of the exhaust from an automotive engine, the exhaust gas flowing along the path passes through the holes 18 of the protective cover 17 and comes into contact with the oxygen sensor element A, whereby a differential partial pressure develops between the equilibrium oxygen partial pressure $P_{O2}$ of the solid pole 1 and the oxygen partial pressure $P'_{O2}$ of the exhaust gas to be measured which causes an electromotive force to be generated according to the formula:

$$E = \frac{RT}{nF} \ln \frac{P'^{o}_{2}}{P^{o}_{2}} \qquad \text{(Nernst formula)}$$

wherein
R: gas constant
T: absolute temperature
F: Faraday constant

Measurement of this electromotive force gives the oxygen concentration in the area to be measured.

The performance of the sensor element can be evaluated by He-leak test, the conductivity test, the autoclave method, the response test and the appearance test.

He-leak test

A specimen (sensor element) 20 is placed on O-rings (silicone rubber + silicone grease) 21, 21 as indicated in FIG. 7 and He-gas is blasted around them. In this state, air is sucked in the direction of the arrow shown in FIG. 7 and the He-concentration in the gas sucked is analyzed by a He-detector (not shown) for evaluation of the gas/tightness of the element itself.

Autoclave method

As indicated in FIG. 8, a solid pole oxygen sensor 22 assembled with the sensor element A according to the present invention is set at the center of a tube 24 with both ends closed by the electromagnetic valves 23, 23', and a DC voltmeter 25 is connected to the sensor 22. Heaters 26 are installed around the tube 24. The atmosphere in the tube 24 is held at about 500° C. by the heater 26, while the air is pressurized to, say, 5 Kg/cm², by one of the valves 23. A change in the electromotive force developed thereby is measured by the DC voltmeter 25. Normally, the oxygen partial pressure difference rises with pressurization, causing a higher electromotive force, but the electromotive force will drop when the sealing is poor and the deterioration advances.

Response Test

FIG. 9 is a diagram illustrating the response characteristic of the solid pole oxygen sensor as the oxygen concentration in the exhaust gas changes. Under rich-→lean (R→L) lean→rich (L→R) changes of the gasoline burning conditions, the electromotive force changes from 0.3 V to 0.6 V or vice versa. The time taken for this change is set as T(R→L), T(L→R). As deterioration begins after long service, T(R→L), T(L→R) become slow. The best condition is that both T(R→L) and T(L→R) are fast and the time change is negligible before and after long service.

Test example 1 - - - lead wire diameter and Rh addition

Using lead wires of Pt and Pt/Rh, their performances depending on the diameter (mm$\phi$) of the lead wires and the additional amount of Rh (% by weight) were investigated. The results are summarized in Tables 1 and 2. The molding pressure was set at 1200 Kg/cm$^2$.

TABLE I

| Wire diameter | | | | |
|---|---|---|---|---|
| Wire diameter (mm$\phi$) | 0.05 | 0.1 | 0.2 | 0.3 |
| Pt | Δ*1 | O | O | Δ*2 |

TABLE 2

| Content of Rh added | | | | | | |
|---|---|---|---|---|---|---|
| Content of Rh added (% by weight) Wire diameter | 10 | 15 | 20 | 25 | 35 | 40 |
| 0.1 mm$\phi$ | Δ*3 | O | O | O | Δ*4 | X |

The rating in the above tables are as follows:
O good
Δ marginally usable
X unfit for use
*1 no snapping of wire, but poor heat resistance
*2 Pt wire and solid electrolyte incompatible; sinterability of wire-surrounding solid electrolyte inferior
*3 wire flexibility reduced resulting in poor moldability
*4 wire hardness increased and elasticity decreased, making the wire unfit for use Test example 2 - - - presence of electroconductive paste Performances of an element (I) applied with electroconductive paste and an element (II) applied with no paste at start of use and after long service (*5) were evaluated by the response test, He-leak test, and autoclave method (air pressurization). The results are summarized in Table 3.

TABLE 3

| | Presence of electroconductive paste | | | | | |
|---|---|---|---|---|---|---|
| Items | Response | | He-leak | | Autoclave | |
| Element | Start | After *5 long service | Start | After *5 long sercive | Start | After *5 long service |
| I | O | O | O | O | O | O |
| II | O | X | O | X | O | X | where *5 durability test condition
= 10 mode run patterns × 200 hours

Test example 3 - - - Molding pressure

The durability of molded products obtained under different molding pressures of Table 4 was evaluated after firing by the appearance test, response test, He-leak test and autoclave method to measure the effect of the molding pressure. The results are summarized in Table 4.

TABLE 4

| | Effect of molding pressure | | | | | | | |
|---|---|---|---|---|---|---|---|---|
| Item | Appearance after firing | | Response | | He-leak | | Autoclave | |
| Pressure (Kg/cm$^2$) | Start | After long service | Start | After long service | Start | After long service | Start | After long service |
| 600 | O | Δ | Δ | X | Δ | X | Δ | X |
| 1000 | O | O | O | Δ | O | Δ | O | Δ |
| 1200 | O | O | O | O | O | O | O | O |
| 1500 | O | O | O | O | O | O | O | O |
| 2000 | O | O | O | O | O | O | O | O |
| 2200 | X | X | X | X | X | X | X | X | where
O good
Δ occasionally rejected
X unfit for use (with deterioration)

It is evident from the above that the oxygen sensor according to the present invention, having its solid pole wrapped in a solid electrolyte and being low-temperature fired after molded, needs no calcining or high-temperature firing of the solid electrolyte.

The structure of the invention can be miniaturized and the manufacturing process can be simplified, because an electroconductive sealing agent is applied to the lead wire buried in the solid pole, the generation of the electromotive force is good, and moreover, with good sealing, the durability is considerably high.

What we claim is:

1. A solid pole oxygen sensor comprising:
   a substantially cylindrical ceramic insulator having electroconductive zones; and
   an oxygen sensor element joined to one end of the insulator and comprising:
   a solid pole coated with an electroconductive paste forming a solid electrode;
   a lead wire, one end of which is at least partially coated with a sealing agent is buried in the solid pole, said lead wire being made of Pt or Pt-Rh; and
   a solid electrolyte in which the solid electrode is encased, the other end of said lead wire being adjacent the periphery of the solid electrolyte.

2. A solid pole oxygen sensor as claimed in claim 1, wherein the end of said lead wire buried in said solid pole is bent in a substantially circular configuration.

3. A solid pole oxygen sensor as claimed in claim 1, wherein the end of said lead wire buried in said solid pole is substantially straight.

4. A solid pole oxygen sensor as claimed in claim 2 or 3, wherein the surface of said lead wire is coated with an electroconductive paste.

5. A solid pole oxygen sensor as claimed in claim 4, wherein:
the entire surface of the lead wire exterior of the solid pole is coated with the electroconductive paste.

6. A solid pole oxygen sensor as claimed in claim 4, wherein:
only part of the surface of the lead wire exterior of the solid pole is coated with the electroconductive paste.

7. A solid pole oxygen sensor as claimed in claim 2 or 3, further comprising:
an outwardly opening recess defined in the solid electrolyte, the other end of the lead wire extends into said recess; and
said recess is filled with an electroconductive paste.

8. A solid pole oxygen sensor as claimed in claim 1, wherein the solid pole is made of Co/CoO, V/Vo or Fe/FeO with other additives.

9. A solid pole oxygen sensor as claimed in claim 1, wherein the lead has a diameter in the range of 0.05–0.5 mm$\phi$.

10. A solid pole oxygen sensor comprising:
a substantially cylindrical ceramic insulator having electroconductive zones; and
an oxygen sensor element joined to one end of the insulator and comprising:
a substantially cylindrical solid pole coated with an electroconductive paste;
a lead wire, one end of which is buried in the solid pole, said lead wire coated with a sealing agent, said lead wire being made of Pt or Pt-Rh; and
a substantially cylindrical solid electrolyte in which the solid pole is encased, the other end of said lead wire extending directly from the solid pole and terminating adjacent the periphery of the solid electrolyte, said electrolyte being substantially longer than and being of substantially greater diameter than said solid pole.

11. A method of manufacturing a solid pole oxygen sensor, said method comprising:
burying one end of a lead wire made of Pt or Pt-Rh and coated with a sealing agent over a portion of said one end in a solid pole;
coating the surface of the solid pole with an electroconductive paste;
encasing the solid pole in a solid electrolyte;
pressure-molding the solid electrolyte with the solid pole encased therein under a pressure of 600 to 2000 Kg/cm$^2$;
drying the solid electrolyte with the solid pole encased therein;
firing the pressure-molded solid electrolyte with the solid pole therein at about 1350°–1500° C. in a reducing atmosphere;
plating or baking Pt electrodes on the surface of the solid electrolyte to form an oxygen sensor element; and
joining the oxygen sensor element to one end of a substantially cylindrical ceramic insulator having electroconductive zones thereon to be connected to the Pt electrodes.

12. A method of manufacturing a solid pole oxygen sensor, said method comprising:
burying one end of a lead wire made of Pt or Pt-Rh in a solid pole, said lead wire being first coated with a sealing agent over a portion of said one end;
coating the surface of the solid pole with an electroconductive paste;
encasing the solid pole in a solid electrolyte;
pressure-molding the solid electrolyte with the solid pole encased therein under a pressure of 600 to 2000 Kg/cm$^2$;
drying the solid electrolyte with the solid pole encased therein;
firing the pressure-molded solid electrolyte with the solid pole therein at about 1350°–1500° C. in a reducing atmosphere; and
plating or baking Pt electrodes on the surface of the solid electrolyte to form an oxygen sensor element.

13. A method of manufacturing a solid pole oxygen sensor, said method comprising:
burying one end of a lead wire made of Pt or Pt-Rh in a substantially cylindrical solid pole, said lead wire being first coated with a sealing agent over a portion of said one end;
coating the surface of the solid pole with an electroconductive paste;
encasing the solid pole in a substantially cylindrical solid electrolyte longer than and of greater diameter than the solid pole with the lead wire extending from the solid pole and terminating at its other end adjacent the periphery of the solid electrolyte;
pressure-molding the solid electrolyte with the solid pole encased therein under a pressure of 600 to 2000 Kg/cm$^2$;
drying the solid electrolyte with the solid pole encased therein;
firing the pressure-molded solid electrolyte with the solid pole therein at about 1350°–1500° C. in a reducing atmosphere; and
plating or baking Pt electrodes on the surface of the solid electrolyte to form an oxygen sensor element.

14. A method of manufacturing a solid pole oxygen sensor, said method comprising:
burying one end of a lead wire made of Pt or Pt-Rh in a solid pole, said lead wire being first coated with a sealing agent over a portion of said one end;
coating the surface of the solid pole with an electroconductive paste;
encasing the solid pole in a solid electrolyte with the lead wire extending from the solid pole and terminating at its other end adjacent the periphery of the solid electrolyte;
pressure-molding the solid electrolyte with the solid pole encased therein under a pressure of 600 to 2000 Kg/cm$^2$;
drying the solid electrolyte with the solid pole encased therein;
firing the pressure-molded solid electrolyte with the solid pole therein at about 1350°–1500° C. for about two to three hours in an atmosphere of inert gas;
plating or baking Pt electrodes on the surface of the solid electrolyte to form an oxygen sensor element; and
joining the oxygen sensor element to one end of a substantially cylindrical ceramic insulator having electroconductive zones thereon to be connected to the Pt electrodes.

* * * * *